(12) United States Patent
Tuccillo

(10) Patent No.: US 8,480,577 B2
(45) Date of Patent: Jul. 9, 2013

(54) WIRELESS PATIENT MONITORING SYSTEM

(75) Inventor: Mark Joseph Tuccillo, Southington, CT (US)

(73) Assignee: Ivy Biomedical Systems, Inc., Branford, CT (US)

( * ) Notice: Subject to any disclaimer, the term of this patent is extended or adjusted under 35 U.S.C. 154(b) by 1101 days.

(21) Appl. No.: 11/205,792

(22) Filed: Aug. 17, 2005

(65) Prior Publication Data
US 2006/0235281 A1 Oct. 19, 2006

Related U.S. Application Data

(60) Provisional application No. 60/672,562, filed on Apr. 18, 2005, provisional application No. 60/671,935, filed on Apr. 15, 2005.

(51) Int. Cl.
*A61B 5/00* (2006.01)
(52) U.S. Cl.
USPC ...... 600/300; 340/539.12; 128/903; 370/908; 370/913
(58) Field of Classification Search
USPC .................. 600/300, 301; 128/903–905, 920
See application file for complete search history.

(56) References Cited

U.S. PATENT DOCUMENTS

| | | |
|---|---|---|
| 3,761,831 A | 9/1973 | Foerster |
| 4,353,372 A | 10/1982 | Ayer |
| 4,588,956 A | 5/1986 | de Corlieu et al. |
| 4,659,872 A | 4/1987 | Dery et al. |
| 4,803,701 A | 2/1989 | Rhodes |
| 4,951,672 A | 8/1990 | Buchwald et al. |
| 4,991,580 A | 2/1991 | Moore |
| 5,217,010 A | 6/1993 | Tsitlik et al. |

(Continued)

FOREIGN PATENT DOCUMENTS

| | | |
|---|---|---|
| EP | 0836864 | 4/1998 |
| JP | 07029430 | 1/1995 |

(Continued)

OTHER PUBLICATIONS

Brunner et al., "Prototype Ventilator and Alarm Algorithm for the NASA Space Station," *Journal of Clinical Monitoring*, 5(2):90-99 (1989).

(Continued)

*Primary Examiner* — Bill Thomson
*Assistant Examiner* — Marie Archer
(74) *Attorney, Agent, or Firm* — K&L Gates LLP

(57) ABSTRACT

A wireless patient monitoring system. In one embodiment the system has a first patient monitoring subsystem including a plurality of sensors and sensor modules; and a processor-transceiver in communication with the plurality of sensors and sensor modules; and a first clinician display subsystem including a processor-transceiver. The processor-transceiver of the first clinician display subsystem broadcasts, on a first predetermined frequency, the frequency the processor-transceiver of the first clinician display subsystem will use to communicate with the processor-transceiver of the first patient monitoring subsystem. The processor-transceiver of the first patient monitoring subsystem then transmits and receives data on the frequency that the processor-transceiver of the first clinician display subsystem will use to communicate with the processor-transceiver of the first patient monitoring subsystem. The processor-transceiver of the first patient monitoring subsystem reverts to the first frequency if communication with the processor-transceiver of the first clinician display subsystem is lost.

10 Claims, 7 Drawing Sheets

U.S. PATENT DOCUMENTS

| | | | |
|---|---|---|---|
| 5,228,450 A * | 7/1993 | Sellers | 600/524 |
| 5,530,701 A * | 6/1996 | Stillman et al. | 370/410 |
| 5,855,550 A * | 1/1999 | Lai et al. | 600/300 |
| 5,862,803 A * | 1/1999 | Besson et al. | 600/508 |
| 6,032,063 A | 2/2000 | Hoar et al. | |
| 6,052,614 A | 4/2000 | Morris et al. | |
| 6,091,296 A | 7/2000 | Rha | |
| 6,100,769 A | 8/2000 | An et al. | |
| 6,640,246 B1 | 10/2003 | Gary, Jr. et al. | |
| 6,897,788 B2 * | 5/2005 | Khair et al. | 340/870.16 |
| 7,088,233 B2 * | 8/2006 | Menard | 340/539.1 |
| 7,373,091 B2 | 5/2008 | Moeller | |
| 7,595,697 B2 | 9/2009 | Tuccillo | |
| 2002/0013518 A1 | 1/2002 | West et al. | |
| 2002/0161308 A1 | 10/2002 | Matsumura et al. | |
| 2003/0174049 A1 | 9/2003 | Beigel et al. | |
| 2004/0077961 A1 | 4/2004 | Yonce | |
| 2004/0176674 A1 | 9/2004 | Nazeri | |
| 2004/0176675 A1 | 9/2004 | Rice et al. | |

FOREIGN PATENT DOCUMENTS

| | | |
|---|---|---|
| JP | 08-140946 | 6/1996 |
| JP | 09-019409 | 1/1997 |
| JP | 10-336075 | 12/1998 |
| JP | 02271149 | 9/2002 |
| WO | 2004086801 A1 | 10/2004 |

OTHER PUBLICATIONS

Shabot, "Standardized acquisition of bedside data: The IEEE P1073 medical information bus," *International Journal of Clinical Monitorirtgand Computing*, 6:197-204 (1989).

Silvern et al., "Ventilator Risk Management Using a Programmed Monitor," *Journal of Clinical Engineering*, 14(3):217-224 (May/Jun. 1989).

PCT Invitation to Pay Additional Fees and Preliminary Search Report of International Searching Authority for International Patent Application No. PCT/US20061013927, mailed Feb. 27, 2007, 8 pages.

PCT International Search Report and Written Opinion of International Searching Authority for International Patent Application No. PCT/US2006/013927, mailed Jun. 5, 2007, 15 pages.

PCT International Search Report and Written Opinion of International Searching Authority for International Patent Application No. PCT/US2006/013616, mailed Aug. 9, 2006, 7 pages.

* cited by examiner

```
struct wordorbyte
{
union {
    unsigned int word;
    struct {
        unsigned char h;
        unsigned char l;
        }bytes;
      }dat;
};

struct txbuf_struct
{
unsigned int ecg;              // 2 ecg
unsigned char key;             // 1 byte for ident id
struct wordorbyte payload;     // 2
};                             // 5 bytes TX total const struct descriptor_struct code descriptor_msg =
{
// ----------------------------------------
// SERIAL NUMBER
//    4 bytes (long)
    0x00,0x00,0x00,0x01,
// ----------------------------------------
// DEVICE TYPE
//    1 byte ? 0=RX, 1=TX
    0x01, // ----------------------------------------
// DEVICE ID
//    1 byte:
//    0x00 : TEST
//    0x01 : 1 channel ECG
//    0x02 : 2 channel ECG, SPO2
//    0x03 : 3 channel ECG, P1
//    0x04 : 4 channel ECG, P1, P2, SPO2
//    0x05 - 0xff: TBD
    0x04,    // 4 channel ECG, P1, P2, SPO2

// ----------------------------------------
// FIRMWARE VERSION
//    4 byte string : "1.00" or any 4 byte ascii chars
    '1','.','0','0',
// ----------------------------------------
// Report Interval
//    00 : Reports only when new data available( not allowed in current
firmware )
//    xx : Number of MS 3,
// ----------------------------------------
//    data_protocol
//
```

FIG 4-1

```
//     00: NO ACK
//     01: ACK with retry
//
       0x01,
// ----------------------------------------
// REPORT BYTES
//     Number of bytes in data report
       5,
// ----------------------------------------
// REPORT DESCRIPTOR IDs
//        ID bytes will be used for each byte in the report
//        0x00 - ECG HIGH BYTE  ( vector 1 )
//        0x01 - ECG LOW BYTE   ( vector 1 )
//        0x02 - Pressure Channel 1 HIGH byte
//        0x03 - Pressure Channel 1 LOW byte
//        0x04 - Pressure Channel 2 HIGH byte
//        0x05 - Pressure Channel 2 LOW byte
//        0x06 - Pressure Channel 3 HIGH byte
//        0x07 - Pressure Channel 3 LOW byte
//        0x08 - Pressure Channel 4 HIGH byte
//        0x09 - Pressure Channel 4 LOW byte
//        0x0a - ECG HIGH BYTE  ( vector 2 )
//        0x0b - ECG LOW BYTE   ( vector 2 )
//        0x0c - Combo: RETRY upper nibble, Packet Count lower nibble
//
//        0x-- RESERVED FOR FUTURE USE
//
//        0xf9 - round robin ID byte
//        0xfa - Packet retry num
//        0xfb - checksum byte high
//        0xfc - checksum byte low
//        0xfd - LENGTH byte
//        0xfe - Packet number byte
//        0xff - mixed DATA type : used in round robin packets
// ----------------------------------------------------------
       0x00,    // ECG1 HIGH
       0x01,    // ECG1 LOW
       0xf9,    // Round Robin ID byte
       0xff,    // Mixed data type
       0xff     // Mixed data type
  );
```

FIG 4-2

WIRELESS PATIENT MONITORING SYSTEM

RELATED APPLICATIONS

This application claims priority to U.S. provisional application 60/672,562 filed Apr. 18, 2005, and U.S. provisional application 60/671,935 filed Apr. 15, 2005, both of which are herein incorporated by reference in their entirety.

FIELD OF THE INVENTION

The invention relates to the field of patient monitoring and more specifically to the field of patient monitoring using wireless communications.

BACKGROUND OF THE INVENTION

The monitoring of patient health parameters is an important aspect of medical care. Typically, this monitoring takes place with the patient physically wired to local devices some of which (for example ECG monitors) may have remote monitoring capabilities. Alternatively, the monitor may be a wireless monitor that communicates only with a transmitter-receiver located in the patient's room.

A problem exists with systems of this type. Specifically, movement of the patient to other locations within the hospital for specialized tests, such as x-ray or endoscopy, requires that patient monitoring cease for a potentially extended period of time. This is hazardous for the patient and results in clinicians not having up-to-date patient information prior to commencing certain procedures. What is required is a means to allow the patient to be continuously monitored without the associated hazards discussed above. The present invention addresses theses issues.

SUMMARY OF THE INVENTION

In one aspect, the invention relates to a wireless patient monitoring system which in one embodiment has a first patient monitoring subsystem including a plurality of sensors and sensor modules; and a processor-transceiver in communication with the plurality of sensors and sensor modules; and a first clinician display subsystem including a processor-transceiver. The processor-transceiver of the first clinician display subsystem broadcasts, on a first predetermined frequency, the frequency that the processor-transceiver of the first clinician display subsystem will use to communicate with the processor-transceiver of the first patient monitoring subsystem. The processor-transceiver of the first patient monitoring subsystem then transmits and receives data on the frequency that the processor-transceiver of the first clinician display subsystem indicated that it will use to communicate with the processor-transceiver of the first patient monitoring subsystem. In another embodiment the processor-transceiver of the first patient monitoring subsystem reverts to the first frequency, if communication with the processor-transceiver of the first clinician display subsystem is lost. In another embodiment, the communication is lost due to patient movement within a hospital.

In yet another embodiment, the wireless system includes a second clinician display subsystem including a processor-transceiver. The processor-transceiver of the first patient monitoring subsystem will establish communications with the processor-transceiver of the second clinician display subsystem when communication with the processor-transceiver of the first clinician display subsystems is lost. In one embodiment the first predetermined frequency and the frequency that the processor-transceivers of first and second clinician display subsystems will use to communicate with the processor-transceiver of the first patient monitoring subsystem are different.

Another aspect of the invention relates to a patient monitoring subsystem for a wireless patient monitoring system having a first clinician display subsystem including a processor-transceiver. The patient monitoring subsystem includes a plurality of sensors and sensor modules; and a processor-transceiver in communication with the plurality of sensors and sensor modules. The first clinician display subsystem broadcasts on a first predetermined frequency a frequency that the processor-transceiver of the first clinician display subsystem will use to communicate with the processor-transceiver of the patient monitoring subsystem. The processor-transceiver of the patient monitoring subsystem then transmits and receives data on the frequency that the processor-transceiver of the first clinician display subsystem will use to communicate with the processor-transceiver of the patient monitoring subsystem.

In one embodiment, the processor-transceiver of the patient monitoring subsystem reverts to the first frequency if communication with the processor-transceiver of the first clinician display subsystem is lost. In another embodiment the communication is lost due to patient movement within a hospital. In another embodiment the wireless system further includes a second clinician display subsystem including a processor-transceiver. The processor-transceiver of the patient monitoring subsystem will establish communication with the processor-transceiver of the second clinician display subsystem when communication with the processor-transceiver of the first clinician display subsystems is lost. In another embodiment, the first predetermined frequency and the frequency that the processor-transceivers of the first and second clinician display subsystems will use to communicate with the processor-transceiver of the patient monitoring subsystem are different.

In another aspect, the wireless system includes a clinician display subsystem for a wireless patient monitoring system. The system in one embodiment includes a first patient monitoring subsystem including a processor-transceiver. The clinician display subsystem includes a processor-transceiver. In one embodiment the processor-transceiver of the clinician display subsystem broadcasts on a first predetermined frequency, the frequency that the processor-transceiver of the clinician display subsystem will use to communicate with the processor-transceiver of the first patient monitoring subsystem. In another embodiment the processor-transceiver of the first patient monitoring subsystem transmits and receives data on the frequency that the processor-transceiver of the clinician display subsystem will use to communicate with the processor-transceiver of the first patient monitoring subsystem.

In another embodiment the processor-transceiver of the patient first monitoring subsystem reverts to the first frequency if communications with the processor-transceiver of the clinician display subsystem is lost. In one embodiment the communications is lost due to patient movement within a hospital. In another embodiment the processor-transceiver of the first patient monitoring subsystem will establish communications with a processor-transceiver of a second clinician display subsystem when communication with the processor-transceiver of the clinician display subsystem is lost. In still yet another embodiment the first predetermined frequency and the frequency that the processor-transceiver of the clinician display subsystem will use to communicate with the processor-transceiver of the patient monitoring subsystem are different.

Yet another aspect of the invention is a method of communicating in a wireless patient monitoring system which in one embodiment includes a first patient monitoring subsystem including a plurality of sensors and sensor modules; and a processor-transceiver in communication with the plurality of sensors and sensor modules; and a first clinician display subsystem. The first clinician display subsystem includes a processor-transceiver. The method includes the steps of broadcasting by the processor-transceiver of the first clinician display subsystem, on a first predetermined frequency, the frequency that the processor-transceiver of the first clinician display subsystem will use to communicate with the processor-transceiver of the first patient monitoring subsystem; and transmitting and receiving by the processor-transceiver of the first patient monitoring subsystem, data on the frequency that the processor-transceiver of the first clinician display subsystem will use to communicate with the processor-transceiver of the first patient monitoring subsystem.

In one embodiment the method includes the step of reverting to the first frequency by the processor-transceiver of the first patient monitoring subsystem if communication with the processor-transceiver of the first clinician display subsystem is lost. In another embodiment the method includes the step of establishing, by the processor-transceiver of the first patient monitoring subsystem, communication with a processor-transceiver of a second clinician display subsystem when communication with the processor-transceiver of the first clinician display subsystem is lost.

BRIEF DESCRIPTION OF THE DRAWING

These and further aspects of the invention can be better understood with reference to the attached specification and drawings in which:

FIG. 4 is an embodiment of a data structure transmitting data according to an embodiment of the protocol of the invention.

DESCRIPTION OF A PREFERRED EMBODIMENT

Figure 1:
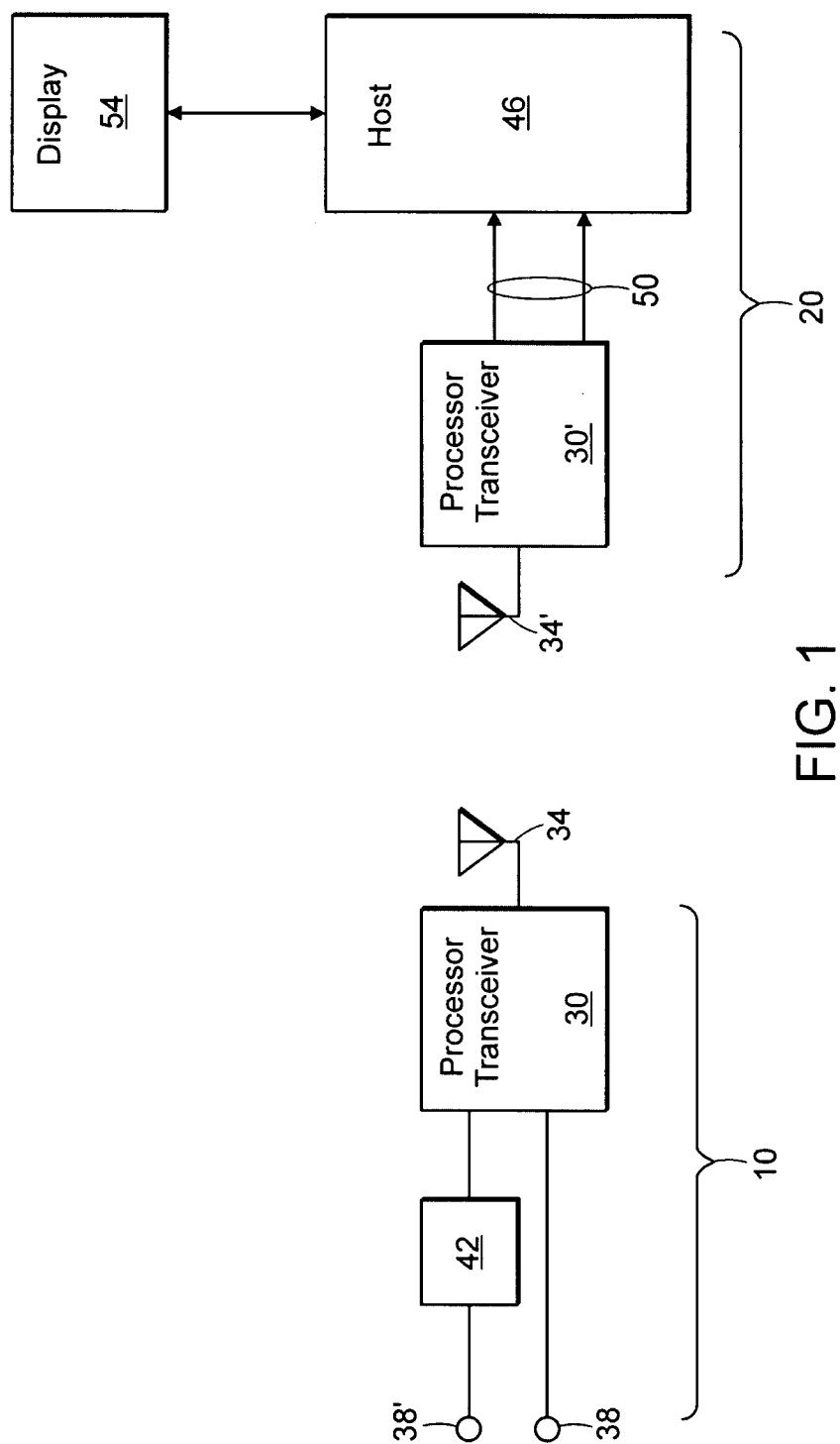
FIG. 1 is a block diagram of an overview of an embodiment of the patient monitoring system of the invention.

In brief overview and referring to FIG. 1, an embodiment of the wireless system of the invention includes a patient monitoring subsystem 10 and a clinician display subsystem 20. The patient monitoring subsystem 10 includes a processor-transceiver 30, an antenna 34 and a series of sensors 38 and sensor modules 42. A sensor module 42 is in communication with a sensor 38' and provides a signal to the processor-transceiver 30 that is not simply the raw sensor signal. The clinician display subsystem 20 includes an antenna 34' in communication with a processor-transceiver 30' which in turn is connected to a host processor 46 by way of UART or distal I/O data ports 50. The data processed by the host processor 46 is displayed to the clinician on a display 54.

Figure 2:
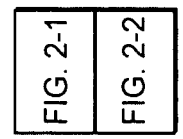
FIG. 2 is a block diagram of an embodiment of the patient monitoring subsystem of the invention.
Figures 1, 2:
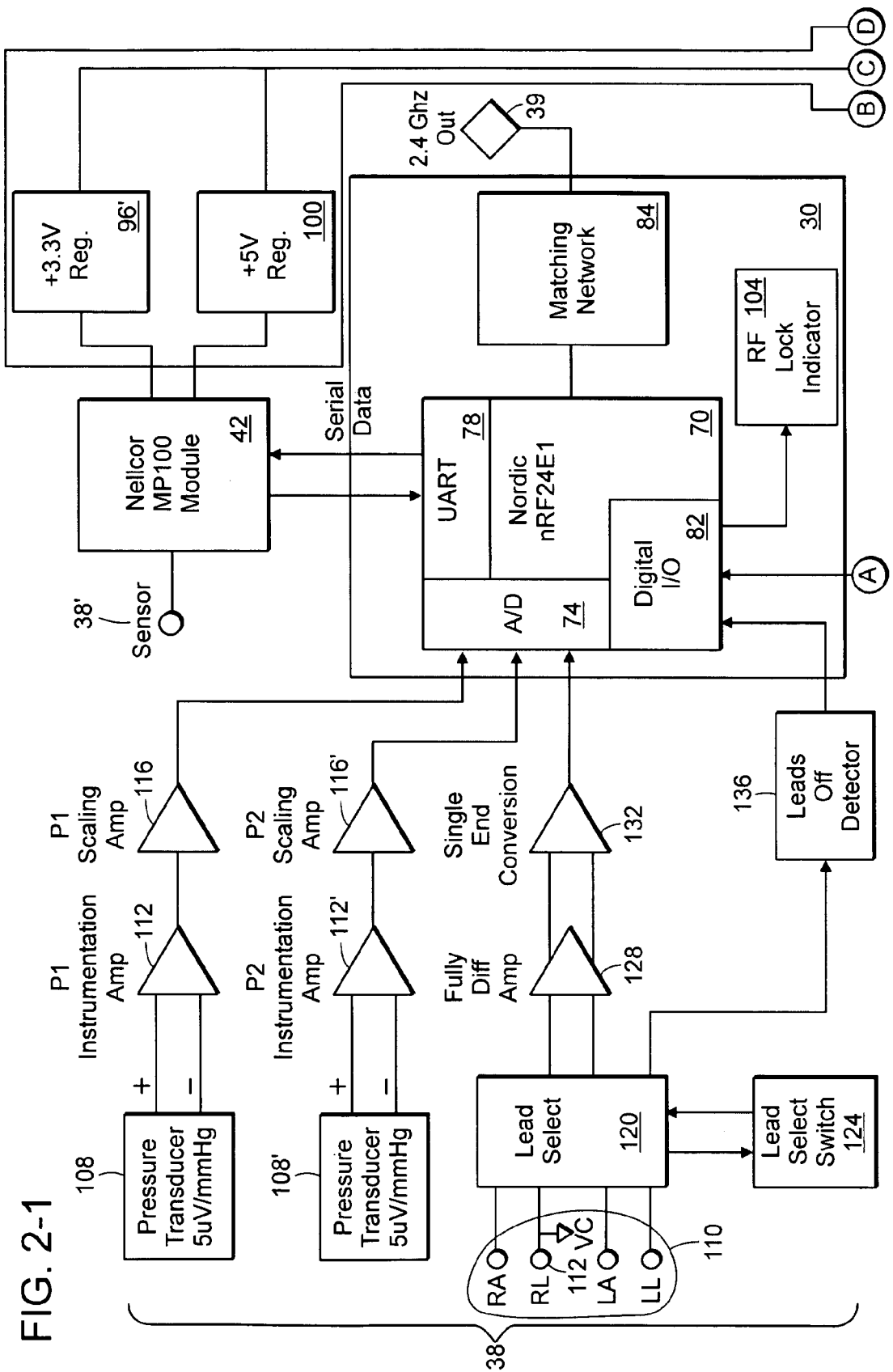
Figure 2:
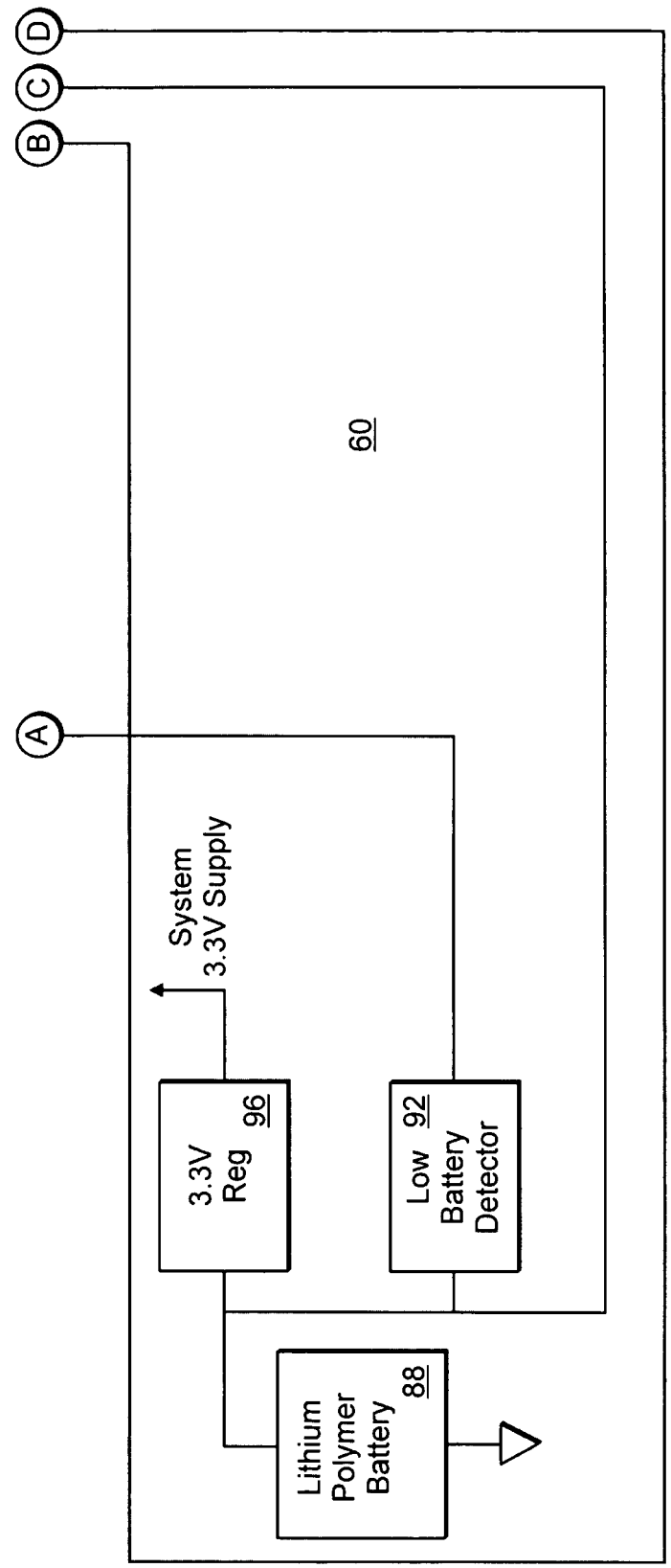

In more detail and referring to FIG. 2, the patient monitoring subsystem 10 of FIG. 1 includes a processor-transceiver 30, a series of sensors 38, sensor modules 42, antenna 34 and power subsystem 60. In the embodiment shown, the processor-transceiver 30 is an nRF24E1 made by Nordic Semiconductor ASA (Tiller, Norway). This device is a 2.4 GHz RF transceiver with an embedded 8051 micro-controller 70, a multi-channel 12 bit A/D converter 74, a UART 78 and a digital I/O port 82. This device has a clock based processor, operates at 1.9 volts and has no external bus.

The transceiver portion of the chip is connected to a matching network 84 to impedance match the antenna 34. The transceiver portion of the chip can be set to operate on any one of 80 frequencies in the 2.4 GHz ISM band.

The power subsystem 60 includes a non-magnetic battery 88 in the form of a lithium polymer, which provides 3.7V at 2.1 A hours and a low battery detector 92 which monitors the battery charge. Two 3.3 V regulators 96, 96' provide regulated voltage to the processor-transceiver 70 and the sensor modules 42. A 5V regulator 100 also provides power to the sensor modules 42 as needed. The integral digital I/O portion 82 both receives input from the low battery detector 92 and also produces an output signal to the RF lock indicator 104 that the RF frequency has been detected and is locked onto.

The embodiment depicted is shown with three sets of sensors 38 and sensor modules 42, but other sensors may be included. The embodiment shown includes two pressure transducers 108, 108'; ECG leads 110; and a pulse oximeter 42. In more detail, the two pressure transducers 108, 108' have a differential output and have resolution of 5 µV/mmHg. The output terminals of the transducers 108, 108' are connected to the respective differential input terminals of instrumentation amplifiers 112, 112'. The respective output terminals of the instrumentation amplifiers 112, 112' are connected to the input terminals of their respective scaling amplifiers 116, 116'. Thus the differential pressure signal monitored by the transducers 108, 108' is converted to a single ended output and amplified. The amplified signal is the input signal to a respective channel of the A/D converter 74.

Similarly, the ECG sensors or leads 110 are connected to a lead select multiplexer 120 which has its control leads controlled by a lead select switch 124 that is settable by the clinician. The lead select switch 124 chooses one of three lead configurations. The first configuration (Lead I) is the differential voltage between the right arm and the left arm leads; the second configuration (Lead II) is the differential voltage between the left leg and the right arm leads; and the third configuration (Lead III) is the differential voltage between the left leg and the left arm leads. The right leg lead 112 is always used as the reference lead. The reference lead acts as a virtual ground, and is at half the regulated power supply or 1.65V.

The output signals from the selected leads are the differential input signals to a differential amplifier 128. The differential output of the differential amplifier 128 is converted by a second differential amplifier 132 to a single ended output. This single ended output signal is the input signal to the A/D converter 74. One output of the lead select multiplexer 120 is the input signal to a leads-off detector 136. The digital output of the leads-off detector 136 is an input signal to the digital I/O port 82. This signal is used to notify the clinician that the leads are not properly placed on the patient.

Figure 2A:
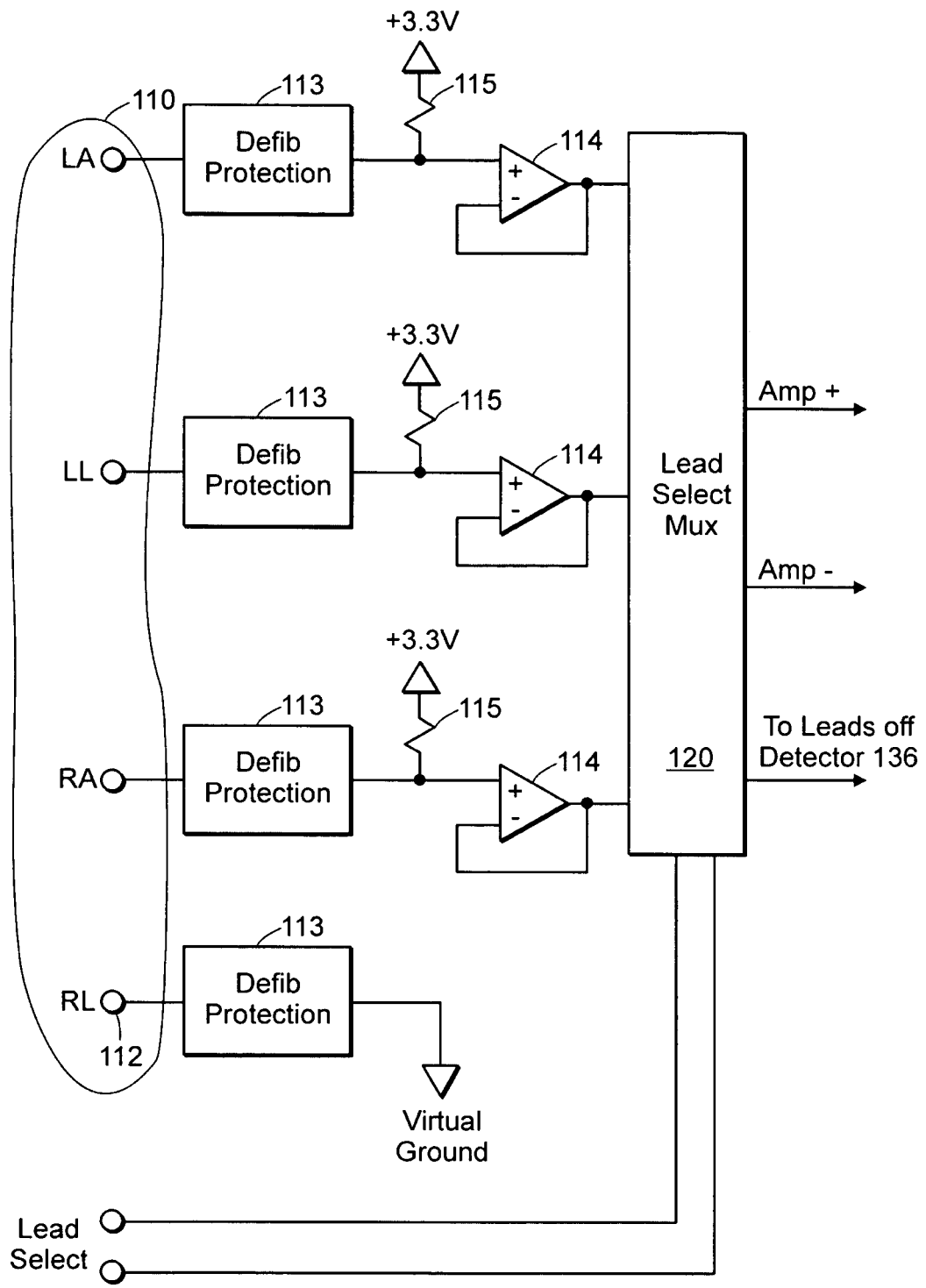
FIG. 2a is a schematic block diagram of an embodiment of the connections between the leads and the lead select multiplexer.

In more detail and referring to FIG. 2a the connections from the leads 110 to the lead select multiplexer 120 is shown in more detail. Each lead 110 is passed through a defibrillation protection circuit (generally 113) prior to being the positive input to a respective buffer amplifier (generally 114). Each leads 110 is pulled to the positive rail by a respective 22M ohm resistor (generally 115), before the lead signal reaches the positive input buffers amplifier 114. The negative input terminal of the input buffer, which is a high impedance unity gain amplifier, is connected to the output terminal of the buffer amplifier 114. If a lead 110 falls off, then the input is open and the voltage at the positive terminal of the buffer amplifier 114 is brought to the positive voltage rail. Within the lead select multiplexer 120, the outputs signals of the buffer amplifiers 114 are diode OR'ed together (not shown) and this in turn is the input signal applied to a voltage comparator (also not shown), which detects when the input voltage reaches about 80% of the reference voltage value. At this point the comparator output transitions and the change of voltage level is detected at the digital I/O port 82 of the processor-transceiver 70.

The A/D converter 74 has enough data acquisition resolution to handle adult ECG data. The digital output of the A/D converter 74 is the input signal to the processor-transceiver 70. The processor portion provides the encoded output signal to the transceiver portion for transmission by the processor-transceiver 70 to the antenna 34 through the matching network 84.

The sensor module 42, in this embodiment a Nellcor MP 100 pulse oximeter, processes data from the sensor 38' and passes the data to the processor-transceiver 70 as serial data. The serial data enters the processor-transceiver 70 through the UART 78.

Figure 3:
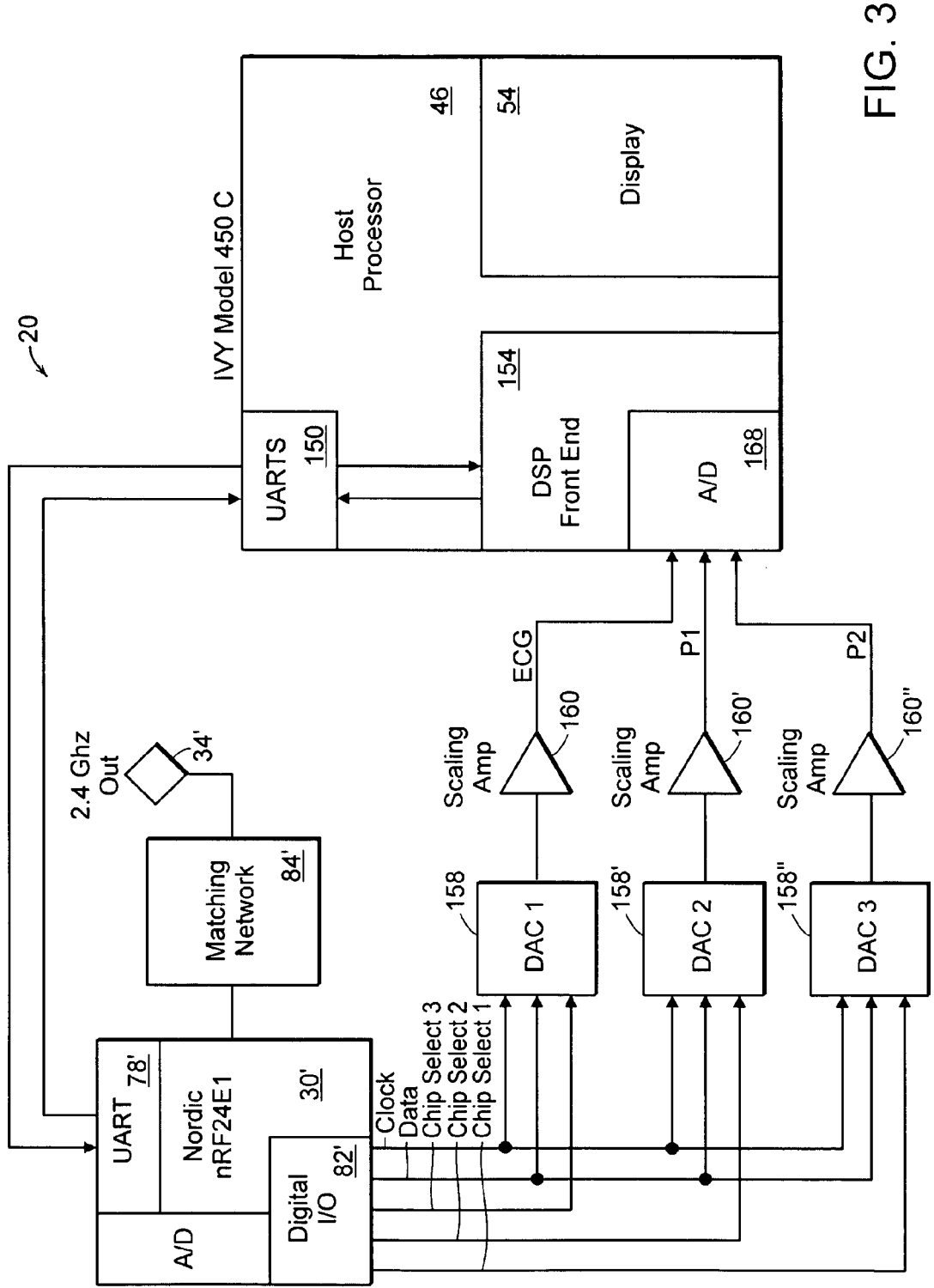
FIG. 3 is a block diagram of an embodiment of the clinician display subsystem of the invention.

Referring to FIG. 3, the clinician display subsystem 20 is shown in more detail. The processor-transceiver 30' in this embodiment is the same Nordic nRF24E1 processor-transceiver 30 that is used in the patient monitoring subsystem 10. As in the patient monitoring subsystem 10, an antenna 34' is connected to the processor-transceiver 30' through a matching network 84'. The received signals are processed by the processor and the results transferred to the host computer 46 by way of the UART 78' or the digital I/O ports 82'. In this embodiment the UART 78' of the processor-transceiver 30' is used to exchange data with the host processor 46 through the host processor UART 150. This data exchange is pre-processed by a digital signal processor front end (DSP) 154 prior to being accessed by the host processor 46 for display on the display 54. In the embodiment shown, oximeter data are transferred in this manner.

The remaining data from the pressure transducers 108, 108' and the ECG leads 110 are transferred to the host processor 46 through the digital I/O port 82'. In this embodiment the digital I/O port 82' provides the data, clock and chip select signals to three digital to analog converters (DAC) 158, 158', and 158" (generally 158). The chip select is used by the digital I/O 82' of the processor-transceiver 30' to select which DAC 158 is to make the conversion from digital to analog. The output signals from each of the DACs 158 are the input signals to respective scaling amplifiers 160, 160', 160" (generally 160). The analog output signals of each of the amplifiers 160 are the input signals to an A/D converter 168 associated with the host processor 46. Thus the ECG, and pressure signals are converted from digital form to analog form and back to digital form for processing by the DSP 154 and host processor 54. The processed output data is used to drive display 54.

Another embodiment is contemplated in which all the data from the processor-transceiver 30' is transferred to the host processor 46 through a digital port on the host system (not shown). Another preferred embodiment places a DSP chip in the patient monitoring subsystem 10, such that the DSP chip and the processor portion of the processor transceiver 30 operate on the data from the sensors 42, and sensor modules 42' before transmitting, to the clinician display subsystem 20, only a reduced amount of data, such as reduced resolution graphical display data. In this way less bandwidth is used in the transmission and less computation needs to occur at the clinician display subsystem 20.

In operation, the patient monitoring subsystem 10 has the processor-transceiver 30 initially in listen mode at a pre-defined frequency. The clinician display subsystem 10 has its processor-transceiver 30' broadcasting on this predetermined frequency, what frequency it will be expecting to transmit and receive on. The processor-transceiver 30 of the patient monitoring subsystem 10, at time zero, will operate in receive mode on channel 0 looking for a response. It will never transmit on any channel until a signal is detected from the processor-transceiver 30' of the clinician display subsystem 20. The processor-transceiver 30 of the patient monitoring subsystem 10 then switches itself to the transmit-and-receive frequency expected by the processor-transceiver 30' of the clinician display subsystem 20. At this point the clinician processor-transceiver 30' instructs the processor-transceiver 30 of the patient monitoring subsystem 10 to collect and transmit data. After each transmission from the processor-transceiver 30 of the patient monitoring subsystem 10, the processor-transceiver 30' of the clinician display subsystem 20 issues an acknowledgement (ACK). If the processor-transceiver 30 of the patient monitoring subsystem 10 fails to receive an ACK it returns to listen mode to determine if the processor-transceiver 30' of the clinician display subsystem 20 has changed transmission frequencies.

Looking at the operation in more detail, the protocol is an ultra low power 2.4 GHz protocol designed for short distance (less then 30 meters) highly deterministic transmission of physiological data from an on-patient instrumentation device to a single receiving and display device. Keep in mind that this simply means that transmission of data from the patient monitoring subsystem to clinician display subsystem is point to point and that any additional networking takes place through the host processor 46. Unlike other ISM band protocols, this protocol is not designed to operate within a network, but in a point to point configuration. As discussed above, it is the function of the processor-transceiver 30' of the clinician display subsystem 20 to display the data and for the host 46 to provide a bridge to a traditional network, such as 10BaseT or 802.11 network, if network transmission is desired. By unburdening the protocol from the need to operate within a network, greater robustness and absolute timing repeatability is achieved.

A feature of the protocol is automatic discovery between any number of patient monitoring subsystems 10 and up to seventy-nine clinician display subsystems within a defined operating environment. The nRF24E1 2.4 GHz transceiver chip with embedded 8051 micro-controller generates a 1 MB burst to transmit up to twenty bytes of data in a packet. The chip employs a sixteen bit CRC for improved data integrity. The chip provides for eighty discrete channels within the 2.4 GHz ISM band, permitting the processor-transceiver 30 of the patient monitoring subsystem 10 initially to be frequency neutral, and adapting to the frequency of the processor-transceiver 30' any clinician display subsystem 20. With this capability a patient could travel from one monitoring environment to another, and the processor-transceiver 30 of the patient monitoring subsystem 10 would automatically lock onto the closest unused clinician monitoring subsystem 20.

For example, prior to entering the operating room, patient preparation could take place in a dedicated room for attaching the sensors and transmitter to the patient. In this room a clinician display subsystem 20 may be present, and this subsystem 20 would be configured to transmit and receive a specific predefined frequency. The processor-transceiver 30 of the patient monitoring subsystem 10, upon powering up, would listen at a predetermined frequency (the neutral frequency) and then discover the actual transmission frequency of the clinician display subsystem 20 and switch to receive it. This would then allow the clinician to verify the quality of the data signals while any medication is given. The patient would then leave the preparation room and travel to the operating room, thus losing the communication ability with the clinician display subsystem 20 in the preparation room. The processor-transceiver 30 of the patient monitoring subsystem 10 would then reset its receive frequency to the neutral frequency again. In the operating room, there would be another clinician display subsystem 20. Again the processor-transceiver 30 of the patient monitoring subsystem 10 would discover the transmission frequency of this new clinician display subsystem 20, set itself to receive this frequency and transmit data.

It is possible to extend the number of devices which can operate within a given clinical zone from seventy nine to about five million by including a sixteen bit address assignment to the processor-transceiver 30 of each clinician display subsystem 20 (equal to seventy nine channels times 65,536). In such an embodiment, multiple clinician display subsystems 20 could operate on the same channel, but would be discriminated by their sixteen bit address. Such an approach is reasonable for implementations requiring low data rates. This is due to the fact that with address discrimination there will be a certain number of radio packet collisions which will require the need for re-transmissions. Furthermore, the transceivers require additional time to decode the packet and to determine if the address matches the assignment. The net effect is a possible reduction in bandwidth.

The combination or protocol and hardware features result in extremely low power consumption; about 13 mW of power when transmitting. The transceivers can send about 100K baud of data in one direction with a real time delay of 3 mS; enough for six physiological parameters. The protocol allows for the re-transmission once of each packet if dropped. It also contains information about signal strength, patient monitoring subsystem 10 processor-transceiver 30 serial number, and battery life. The protocol also allows for about fifty kilobaud of information to be sent from the clinician display subsystem 20 back to the processor-transceiver 30 of the patient monitoring subsystem 10.

In more detail, the processor-transceivers 30, 30' have four operational states. In the first state, State_0, the processor-transceiver 30 is set to the neutral frequency, the frequency at which the processor-transceiver 30 of the patient monitoring subsystem 10 listens for the presence of a clinician display subsystem 20. The processor-transceiver 30' of the clinician display subsystem 20 at this point is broadcasting a low power RF signal (termed a beacon) out every 10 mS on the neutral frequency (channel 0) indicating which channel from one to seventy-nine the processor-transceiver 30' of the clinician display subsystem 20 has been assigned and will be receiving on. The processor-transceiver 30' of each clinician display subsystem 20 within an operating environment has a unique channel assignment. After sending the beacon, the clinician processor-transceiver 30' switches to the assigned channel and listens for a response from the processor-transceiver 30 of the patient monitoring subsystem 10. If no response is received, then the clinician transceiver 30' transmits a beacon again and then again listens for a response. This continues until a response is found. All beaconing happens at −20 dBM, so as to limit the coverage area to about three meters.

Once the processor-transceiver 30' of the clinician display subsystem 20 and the processor-transceiver 30 of the patient monitoring subsystem 10 have established the transmit and receive frequency, the transceivers 30, 30' are in State_1. In this state, the processor-transceiver 30 of the patient monitoring subsystem 10 is switched to the operating channel indicated by the beacon message from the processor-transceiver 30' of the clinician display subsystem 20. The processor-transceiver 30 of the patient monitoring subsystem 10 sends an "ACK" or acknowledgement message. The clinician transceiver 30' transmits an "RFD" or request for descriptor to the patient monitoring subsystem 10 processor-transceiver 30. The processor-transceiver 30 of the patient monitoring subsystem 10 responds with another "ACK". From here on, any received message in either direction will be responded to with an "ACK".

At this point the transceivers 30, 30' have entered State_2. This is the discovery state of the system. The processor-transceiver 30 of the patient monitoring subsystem 10 will now tell the processor-transceiver 30' of the clinician display subsystem 20 about itself. The processor-transceiver 30 of each patient monitoring subsystem 10 has a hard coded unique thirty two bit serial number in read only memory which is also displayed on the patient monitoring subsystem's 10 enclosure as a six decimal digit value. The processor-transceiver 30 of the patient monitoring subsystem 10 now sends this serial number to the clinician display subsystem 20, for display and awaits the "ACK" message from the clinician transceiver 30'. All communications now occurs at full RF power or 0 dBM. Every message received from the processor-transceiver 30 of the patient monitoring subsystem 10 is acknowledged by the clinician transceiver 30' with an "ACK" message. In this state, if the processor-transceiver 30 of the patient monitoring subsystem 10 receives no "ACK" from the clinician transceiver 30', it will re-transmit its previous message thirty two times, and after which it will assume that it is no longer in contact with the clinician transceiver 30' with which it had been in contact and looks for another clinician transceiver 30' by returning to State_0.

If the clinician display subsystem 20 has received a response from the processor-transceiver 30 of a patient monitoring subsystem 10 that is compatible, the clinician display subsystem 20 processor-transceiver transmits a "GTD" or go-to-data message and the processor-transceiver 30 of the patient monitoring subsystem 10 returns an "ACK". The processor-transceiver 30 of every patient monitoring subsystem 10 includes a bi-color red-green LED 104 to indicate the state it is operating in; red for communications with the clinician transceiver 30' (termed a "no-lock") and green for communications with the clinician transceiver 30' (termed a "lock"). At this point the processor-transceiver 30 of the patient monitoring subsystem 10 lights the green LED, and the transceivers 30, 30' enter State_3. Patient data transmission begins. If the clinician display transceiver 30' is not expecting to communicate with the transmitting processor-transceiver 30 of the patient monitoring subsystem 10, the clinician transceiver 30' sends a "DNC" or device-not-compatible message. The processor-transceiver 30 of the patient monitoring subsystem 10 then sends an "ACK" and both devices return to State_0. The processor-transceiver 30 of a patient monitoring subsystem 10, having received a "DNC", will delay for 15 seconds before entering State_0, to allow another local patient monitoring subsystem 10, if present, a chance to lock onto the clinician display transceiver 30'.

In State_3 the continuous data transfer takes place. The basic cycle time is three mS, in which a data packet of up to nineteen bytes is sent from the processor-transceiver 30 to the patient monitoring subsystem 10 to the clinician display transceiver 30', and an "ACK" is sent from the clinician display transceiver 30' back to the processor-transceiver 30 of the patient monitoring subsystem 10. All this takes about 1.2 mS, which leaves enough time for the processor-transceiver 30 of the patient monitoring subsystem 10 to re-transmit the last packet if no "ACK" is received within 500 uS of sending the packet. This data transmission sequence is repeated as long as the processor-transceiver 30 of the patient monitoring subsystem 10 receives an "ACK", and the system allows for the re-transmission of one missed packet. Due to the real time nature of the signals being transmitted and the fact that the system must be deterministic, after retransmitting the missed packet, the system must move on to the next data point if the re-transmitted packet is also lost. At the clinician monitoring missed data points are interpolated. In most cases two or three missed data points in a row will not affect the ability to process the signal. If the clinician display transceiver 30 goes for more then 5 seconds without receiving an "ACK", it will then return to State__0.

Referring to FIG. 4, the data structure is shown for on-patient monitoring suitable for an operating room, in which four parameters are sent: one twelve bit ECG vector at a three mS sampling period, two to twelve bit Invasive Pressure signals at a 25 mS sample rate, and the digital stream from the Nellcor MP-100 module.

With the protocol shown additional modules and sensors can be added to meet the needs of the clinician.

The embodiments shown are exemplary and one skilled in the art will realize that modifications and changes may be made without deviating from the spirit of the invention. The invention is intended to be limited only by the scope of the attached claims.

I claim:

1. A wireless patient monitoring system comprising:
   a first patient monitoring subsystem comprising:
      a plurality of sensors and sensor modules;
      and a processor-transceiver in communication with said plurality of sensors and sensor modules; and
   a plurality of clinician display subsystems, each clinician display subsystem comprising a respective processor-transceiver and having a pre-assigned channel,
   wherein said processor-transceiver of each of said plurality of clinician display subsystems broadcasts on a first predetermined frequency the respective pre-assigned channel that said processor-transceiver of said clinician display subsystem will use to communicate with said processor-transceiver of said first patient monitoring subsystem; and
   wherein said processor-transceiver of said first patient monitoring subsystem transmits and receives data on said respective pre-assigned channel that said processor-transceiver of one of said plurality of clinician display subsystem will use to communicate with said processor-transceiver of said first patient monitoring subsystem.

2. The wireless system of claim 1 wherein said processor-transceiver of said first patient monitoring subsystem reverts to said first frequency if communication with said processor-transceiver of said current clinician display subsystem is lost.

3. The wireless system of claim 2 wherein said communication is lost due to patient movement within a hospital and wherein the data is transmitted using a protocol that is designed to operate over a distance less than 30 meters.

4. The wireless patient monitoring system of claim 1 wherein said plurality of sensors and sensor modules comprise an ECG monitor and an oximeter.

5. The wireless patient monitoring system of claim 4 wherein the ECG monitor comprises a plurality of leads and said leads are selectable by a clinician.

6. The wireless patient monitoring system of claim 5 wherein the ECG monitor comprises a differential amplifier in communication with a single ended amplifier in communication with a switch multiplexer.

7. A method of communicating in a wireless patient monitoring system comprising a first patient monitoring subsystem comprising a plurality of sensors and sensor modules; and a processor-transceiver in communication with said plurality of sensors and sensor modules; and a plurality of clinician display subsystems, each of said clinician display subsystems comprising: a respective processor-transceiver and having a respective pre-assigned channel, said method comprising the steps of:
   broadcasting by said processor-transceiver of each of said clinician display subsystems, on a first predetermined frequency its respective pre-assigned channel that said processor-transceiver of first respective clinician display subsystem will use to communicate with said processor-transceiver of said first patient monitoring subsystem; and
   transmitting and receiving, by said processor-transceiver of said first patient monitoring subsystem, data on said pre-assigned channel that said processor-transceiver of said respective clinician display subsystem will use to communicate with said processor-transceiver of said first patient monitoring subsystem.

8. The method of claim 7 further comprising the step of reverting to said first frequency by said processor-transceiver of said first patient monitoring subsystem if communication with said processor-transceiver of said first current clinician display subsystem is lost.

9. The method of claim 8 further comprising the step of establishing, by said processor-transceiver of said first patient monitoring subsystem, communication with a processor-transceiver of another clinician display subsystems when communication with said processor-transceiver of said current clinician display subsystem is lost.

10. The method of claim 8 wherein said communication with said processor-transceiver of said first current clinician display subsystem is determined to be lost by said processor-transceiver of said first patient monitoring subsystem if no ACK is received from said current clinician display subsystem.

* * * * *